(12) United States Patent
Shahrestani et al.

(10) Patent No.: US 12,414,708 B2
(45) Date of Patent: Sep. 16, 2025

(54) EDDY CURRENT DAMPING RESPIRATORY WAVEFORM AND VOLUME SENSOR

(71) Applicant: California Institute of Technology, Pasadena, CA (US)

(72) Inventors: Shane S. Shahrestani, Yorba Linda, CA (US); Tzu-Chieh Chou, Pasadena, CA (US); Yu-Chong Tai, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 896 days.

(21) Appl. No.: 17/534,267

(22) Filed: Nov. 23, 2021

(65) Prior Publication Data

US 2022/0160254 A1 May 26, 2022

Related U.S. Application Data

(60) Provisional application No. 63/117,924, filed on Nov. 24, 2020.

(51) Int. Cl.
*A61B 5/08* (2006.01)
*A61B 5/087* (2006.01)
*A61B 5/097* (2006.01)

(52) U.S. Cl.
CPC .............. *A61B 5/082* (2013.01); *A61B 5/087* (2013.01); *A61B 5/097* (2013.01)

(58) Field of Classification Search
CPC ......... A61B 5/082; A61B 5/087; A61B 5/097; A61B 5/05; A61B 5/0816; A61B 5/1135
See application file for complete search history.

(56) References Cited

U.S. PATENT DOCUMENTS

| | | | |
|---|---|---|---|
| 6,435,182 B1 * | 8/2002 | Lutchen | A61B 5/085 128/200.24 |
| 11,890,097 B2 | 2/2024 | Tai et al. | |

(Continued)

OTHER PUBLICATIONS

A. Richer and A. Adler, "Eddy Current Based Flexible Sensor for Contactless Measurement of Breathing," 2005 IEEE Instrumentation and Measurement Technology Conference Proceedings, Ottawa, ON, Canada, 2005, pp. 257-260, doi: 10.1109/IMTC.2005.1604112. (Year: 2005).*

(Continued)

*Primary Examiner* — Daniel L Cerioni
*Assistant Examiner* — Kavya Shobana Balaji
(74) *Attorney, Agent, or Firm* — Mark P. Mathison (57) ABSTRACT

Medical diagnostic devices and related methods of use are described in which a sensor coil may be connected with a resistive, inductive, and capacitive (RCL) circuit including a power meter and a frequency counter, and the sensor may be positioned on a chest of a subject. The sensor apparatus may apply an alternating current through the sensor coil. The sensor apparatus may measure parallel resistance values in the sensor coil using the power meter for a time interval while the subject inhales and exhales. The sensor apparatus may record the parallel resistance values. The sensor apparatus may determine a first change in the parallel resistance values by measuring a difference between a crest and a trough of the parallel resistance values, wherein the crest of the parallel resistance value corresponds to the inhale and the trough of the parallel resistance value corresponds to the exhale of the subject's breath.

16 Claims, 10 Drawing Sheets

(56) References Cited

U.S. PATENT DOCUMENTS

| | | | |
|---|---|---|---|
| 2013/0172759 A1* | 7/2013 | Melker | A61B 5/682 600/476 |
| 2015/0038805 A1* | 2/2015 | Bhargava | A61B 5/4205 600/593 |
| 2017/0035304 A1* | 2/2017 | Shiau | A61B 5/0878 |
| 2020/0082926 A1 | 3/2020 | Tai et al. | |
| 2021/0251546 A1 | 8/2021 | Tai et al. | |

OTHER PUBLICATIONS

D. Teichmann, J. Foussier, J. Jia, S. Leonhardt and M. Walter, "Noncontact Monitoring of Cardiorespiratory Activity by Electromagnetic Coupling," in IEEE Transactions on Biomedical Engineering, vol. 60, No. 8, pp. 2142-2152, Aug. 2013, doi: 10.1109/TBME.2013.2248732. (Year: 2013).*

Ojarand, J., Pille, S., Min, M., Land, R., & Oleitšuk, J. (2015). Magnetic induction sensor for the respiration monitoring. In Proc. of 10th Int. Conf. on Bioelectromagnetism (icBEM). Tallinn (pp. 1-4). (Year: 2015).*

Guardo, Robert & Charron, Guy & Goussard, Yves & Savard, Pierre. (1997). Contactless measurement of thoracic conductivity changes by magnetic induction. 6. 2450-2453 vol. 6. 10.1109/IEMBS.1997.756820. (Year: 1997).*

S. Liu, R. X. Gao, Q. He, J. Staudenmayer and P. Freedson, "Development of statistical regression models for ventilation estimation,"2009 Annual International Conference of the IEEE Engineering in Medicine and Biology Society, Minneapolis, MN, USA, 2009, pp . 1266-1269, doi: 10.1109/IEMBS.2009.5333890 (Year: 2009).*

Eastwood-Sutherland, T. J. Gale, P. A. Dargaville and K. Wheeler, "Non-contact respiratory monitoring in neonates," The 7th 2014 Biomedical Engineering International Conference, Fukuoka, Japan, 2014, pp. 1-5, doi: 10.1109/BMEICON.2014.7017373. (Year: 2014).*

Al-Khalidi et al., "Respiration Rate Monitoring Methods: A Review", Pediatric Pulmonology, vol. 46, No. 6, Jun. 2011, pp. 523-529.

Celli et al., "Standards for the Diagnosis and Treatment of Patients with COPD: A Summary of the ATS/ERS Position Paper", The European Respiratory Journal: Official Journal of the European Society for Clinical Respiratory Physiology, vol. 23, No. 6, Jun. 2004, pp. 932-946.

Chu et al., "Respiration Rate and Volume Measurements Using Wearable Strain Sensors", Nature Partner Journals, Available Online at: https://doi.org/10.1038/s41746-019-0083-3, Feb. 13, 2019, 9 pages.

Crimi et al., "Practical Considerations for Spirometry during the COVID-19 Outbreak: Literature Review and Insights", Pulmonology, vol. 27, No. 5, Available Online at: https://doi.org/10.1016/j.pulmoe.2020.07.011, Aug. 2020, 11 pages.

Dodd et al., "Analytical Solutions to Eddy-Current Probe-Coil Problems", Journal of Applied Physics, vol. 39, No. 6, May 1968, pp. 2829-2838.

Falliers , "Letter: Self-Measurements for Asthma", JAMA: The Journal of the American Medical Association, vol. 230, No. 4, Oct. 28, 1974, pp. 537-538.

Jindal et al., "Problems of Management of Non-Corona Respiratory Diseases in the Era of COVID-19", International Journal of Noncommunicable Diseases, vol. 5, No. 2, Jan. 2020, pp. 63-69.

Lombardi et al., "Rethinking Respiratory Function Laboratories in the Era of Coronavirus Disease 2019: Considerations for Today and the Day After", Annals of Allergy, Asthma & Immunology: Official Publication of the American College of Allergy, Asthma, & Immunology, vol. 125, No. 2, May 2020, 3 pages.

Mimoz et al., "Accuracy of Respiratory Rate Monitoring Using a Non-Invasive Acoustic Method after General Anaesthesia", British Journal of Anaesthesia, vol. 108, No. 5, Feb. 8, 2012, pp. 872-875.

Phan et al., "Estimation of Respiratory Waveform and Heart Rate Using an Accelerometer", Conference Proceedings: Annual International Conference of the IEEE Engineering in Medicine and Biology Society, IEEE Engineering in Medicine and Biology Society, Conference 2008, Aug. 20-24, 2008, pp. 4916-4919.

Redding et al., "Lung Function in Children Following Empyema", American Journal of Diseases of Children, vol. 144, No. 12, Dec. 1990, pp. 1337-1342.

Wong et al., "Practical Considerations for the Diagnosis and Treatment of Fibrotic Interstitial Lung Disease during the COVID-19 Pandemic", Chest, vol. 158, No. 3, Available Online at: https://www.sciencedirect.com/science/article/pii/S001236922030756X, Sep. 2020, pp. 1069-1078.

* cited by examiner

EDDY CURRENT DAMPING RESPIRATORY WAVEFORM AND VOLUME SENSOR

CROSS-REFERENCES TO RELATED APPLICATIONS

The present application claims the benefit of U.S. Provisional Application No. 63/117,924, filed Nov. 24, 2020, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Art

Embodiments of the present invention generally relate to diagnostic instruments, implements, and processes using magnetic field sensors for in vivo measurements. Specifically, they relate to medical devices that measure lung function through measuring parallel resistance values in an electrical circuit coupled with a magnetic field through the brain.

2. Description of the Related Art

Pulmonary function testing (PFT) involves comprehensive evaluation of the lungs to provide objective and quantifiable metrics for pulmonary function. Oftentimes, PFTs are indicated when the clinician suspects obstructive lung disease, such as chronic obstructive pulmonary disease (COPD) and asthma, or restrictive lung disease, such as pulmonary fibrosis or sarcoidosis. In contemporary clinical practice, PFTs are most commonly performed using spirometry, and occasionally with lung plethysmography.

As these current methods require examination and monitoring of breathing, they present inherent risks to physicians and other health professionals of exposure to airborne diseases. For example, the American Thoracic Society and many comparable international societies have recommended postponing PFTs during the coronavirus disease 2019 (COVID-19) pandemic, due to the high risk of COVID-19 transmission during a testing visit. While these restrictions were put in place through expert guidance to prevent the spread of disease, the restrictions have made it difficult to gauge pulmonary function in patients with previously diagnosed lung disease as well as those patients recovering from COVID-19 pneumonia whom require close follow-up examination.

Other devices have been contemplated which utilize accelerometers to characterize the respiratory waveform through anteroposterior displacement of the thorax during breathing. Further groups have developed acoustic-based sensors that monitor air movement near the nose, or air moving through an airway, to monitor respiration. Similarly, mechanical strain sensors, placed on the chest like a piece of tape, have been implemented by some groups to accurately measure the respiratory waveform in addition to approximation of non-statistically significant ratios of forced expiratory volume in one second (FEV1) and forced vital capacity (FVC). However, many of these sensors fail to accurately gauge both respiration volume and relevant pulmonary metrics, and the strain-based sensors often require calibration and tight contact with the subject's skin in order to yield accurate results.

Therefore, there is a need in the art for alternative technologies and methods to perform PFT testing which may reduce risk of incidental exposure to airborne pathogens and which are also easy to use and accurate in measuring respiration volume and relevant pulmonary metrics.

BRIEF SUMMARY

A sensor apparatus is described for pulmonary function testing and other diagnostics in the lungs, and methods of use of the same. The apparatus may include an inductive device including a sensor coil and a resistive, inductive, and capacitive (RLC) circuit with a power meter and a frequency counter. The components fashion a resonant circuit. When positioned on the chest of a subject, a periodic current (such as a sinusoidal alternating current) may be applied through the sensor coil for a time interval while the subject inhales and exhales. The apparatus may be a wearable device and may be a non-contact device.

In one aspect, the resonant coil circuit sensor detects changes to its relatively weak magnetic fields generated by the coil and resultant eddy current damping (ECD) in nearby tissue to track changes in conductivity within the chest cavity during the respiratory cycle. As non-conductive air enters the lungs during inspiration, local measured conductivity decreases. Conversely, expiration decreases the anteroposterior dimension of the chest, putting the coil sensor in closer proximity to conductive vasculature and tissue within the thoracic cavity. As such, the coil sensor can continuously measure parallel resistance ($R_p$) detected within the chest cavity to measure pulmonary function, even while the inductive device is obstructed by clothing. Additionally, implementation of conductivity-based scanning allows for mapping of the conductivity of the thoracic cavity by static or active scanning.

In one aspect, parallel resistance values may be measured in the sensor coil over a time interval. The parallel resistance values may increase and decrease as the subject breathes. Specifically, the parallel resistance values over the time interval vary from a crest and a trough, which correspond with the inhale and the exhale of the subject's breath, respectively. As such, a change in the parallel resistance values may be determined by measuring a difference between a crest and a trough of the parallel resistance values for a given consecutive inhale and exhale.

In one aspect, post-collection data processing (e.g. filtration) may be implemented to improve visibility transitions between inhalation and exhalation. For example, "noise" detected in the sensing process can be removed from the parallel resistance values. Further, the parallel resistance data may be processed into a sinusoidal pulmonary waveform.

Parallel resistance may be measured at a location for a few seconds or longer and collected to determine the respiratory waveform and respiratory rate (RR) of a subject. For example, a change in parallel resistance for one or more breaths (e.g. between an inhale and an exhale) may be calculated and averaged to give a resulting average parallel resistance for a given time interval. In various aspects more breaths may be measured at a location to increase accuracy of the average parallel resistance. In various aspects, the parallel resistance may be measured dynamically by moving the inductive device across the chest of the subject while scanning.

The mean change in parallel resistance per breath has a positive correlation with common industry pulmonary variables. With respect to pulmonary volume metrics, regression analysis demonstrated that the mean change in parallel resistance per breath was closely correlated with FEV1 and FVC. Further parallel resistance per breath has a positive correlation with respiratory rate. Such correlations may allow for a physician or other operator to utilize the parallel resistance values (either directly or indirectly) to diagnose a respiratory problem or respiratory condition.

In one aspect, the apparatus may further include a position gauge attached to the inductive device, wherein the determining of the location at which the measured values are associated with a location on the chest of the subject. The device may include an accelerometer or gyroscope configured to determine the location at which each measured value is taken. The operations can include generating a matrix of exceedances based on measured values from multiple cranial locations.

In one aspect, the inductive device may be positioned at various locations on a subject's chest to record data specific to various regions of the lungs. For example, separate parallel resistance measurements may be taken for each lung, or multiple locations may be used for each lung. In other aspects, the inductive device may be positioned generally in the center of the chest between the lungs and a single location may be utilized to record parallel resistance data. In general, the size of the sensor coil within the inductive device may relate to the desired area of measurement at each location, such that a larger sensor coil may measure more area of the lungs from a single location than a smaller sensor coil.

Reference to the remaining portions of the specification, including the drawings and claims, will realize other features and advantages of embodiments of the present invention. Further features and advantages, as well as the structure and operation of various embodiments of the present invention, are described in detail below with respect to the accompanying drawings. In the drawings, like reference numbers can indicate identical or functionally similar elements.

DETAILED DESCRIPTION

An inductive device placed on the chest or otherwise proximal to the chest cavity may measure parallel resistance values indicative of pulmonary function and respiratory rate. In one aspect, parallel resistance values may be used to create a predicted pulmonary volume metric, such as FEV1 and FVC, and/or respiratory rate. These predicted values may be compared with known ranges to determine or predict a condition or otherwise provide results as to respiratory health. In this way, the parallel resistance value may provide a correlated value which is comparable to a FEV1 or FVC value without a subject necessarily undergoing a spirometry and/or a lung plethysmography, for example.

In one aspect, the parallel resistance may further be utilized as a result metric in itself. For example, various historical parallel resistance values may be acquired from sample subjects, or otherwise from previous uses of the sensor apparatus at similar or same locations of the chest cavity. A measured parallel resistance from a subject may then be compared to the historical parallel resistance values. Any measured parallel resistance value outside of normal ranges may indicate a respiratory condition or respiratory problem.

Unlike a traditional electronic crack detection (ECD) sensor used in the industry, which consist of a bridge circuit that measures its sensor coil impedance, present embodiments have the sensor coil paired with a capacitor to form an electrical resonant circuit. When a conductive target, such as blood, is placed in front of the coil, eddy currents are generated in the target and produce a counteracting magnetic field. This counteracting magnetic field causes a decrease in the coil inductance, or equivalently, a rise in the coil resonant frequency that can be measured by a precise frequency counter.

The same counteracting magnetic field in the target also imposes an electromotive force that impedes the current flow in the coil, thus increasing the sensor coil's alternating current (AC) resistance. The change in coil resistance can be determined by measuring the power dissipation in the coil with a precise power meter. The parallel resistance (R) of the resonant inductive-capacitive (LC) tank is inversely related to the coil's AC resistance by R.

U.S. Patent Application Publication No. US 2020/0082926 A1, published Mar. 12, 2020, further describes fundamentals of an inductive damping sensor and is incorporated herein by reference. U.S. Patent Application Publication No. US 2021/0251546 A1, published Aug. 19, 2021, further describes fundamentals of an inductive damping sensor and is incorporated herein by reference.

A technical advantage of the resonant circuit is low power consumption. This can be of great importance for wearable or otherwise portable, battery-powered sensors. Assuming the chest can be modeled as a flat, two-layer structure (see FIG. 2A), then the coil's AC resistance is related to the tissue conductivity implicitly and can be modeled by a set of analytical solutions.

Figure 1A:
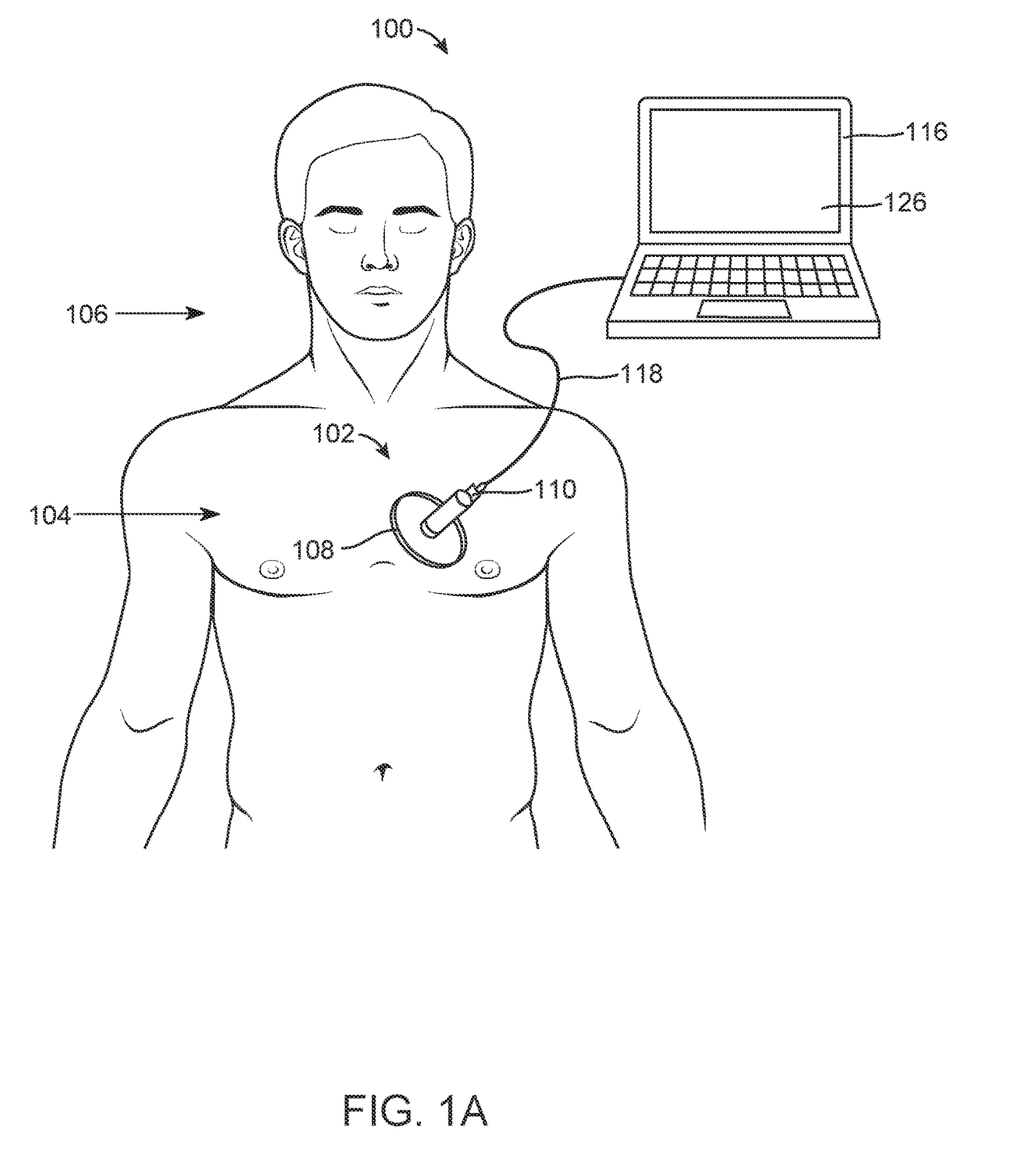
FIG. 1A illustrates an exemplary sensor apparatus for respiratory diagnostics, including an inductive device positioned on a chest of a human subject according to various implementations of the present disclosure.
Figure 1B:
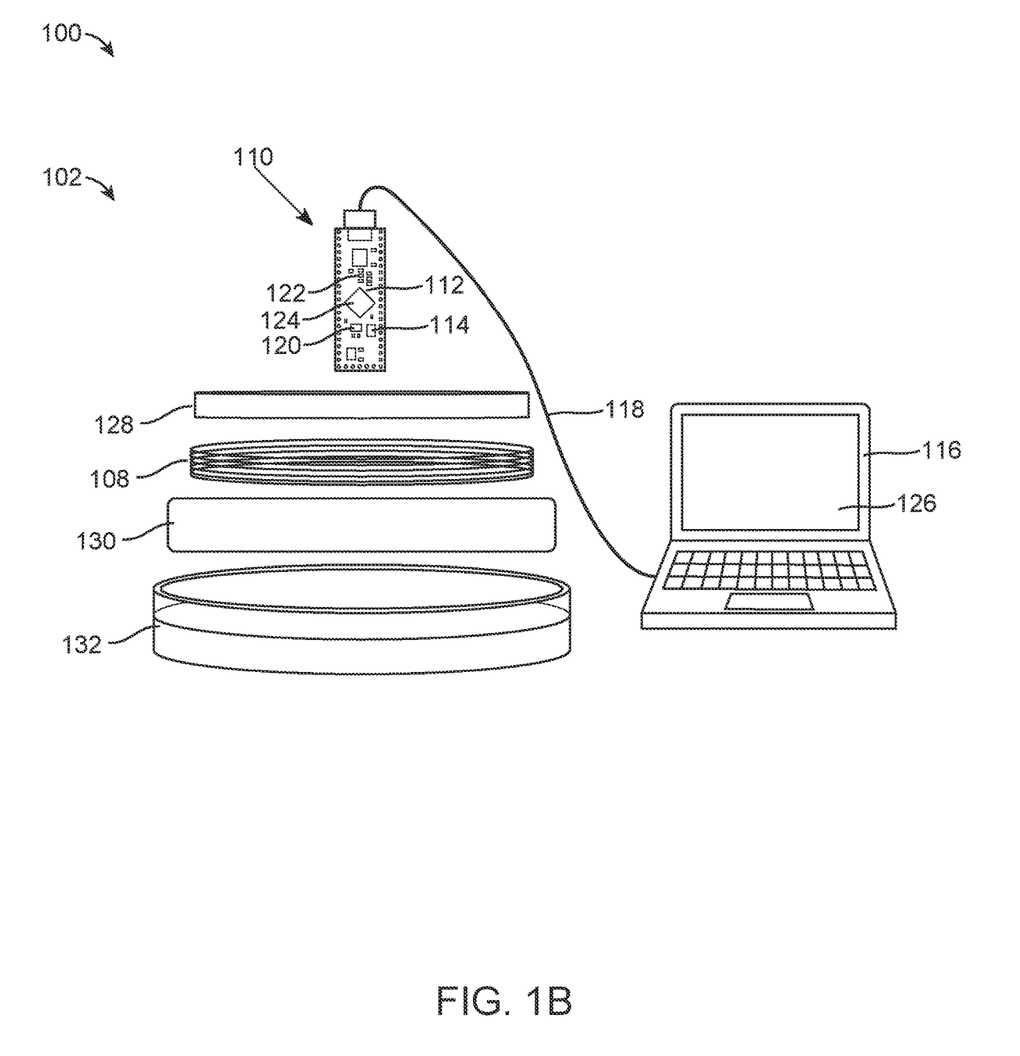
FIG. 1B illustrates an exploded view of the sensor apparatus of FIG. 1.

FIGS. 1A-1B illustrate an exemplary sensor apparatus 100 for respiratory diagnostics, including an inductive device 102 positioned on a chest 104 of a subject 106 according to various implementations of the present disclosure.

The inductive device 102 may include a sensor coil 108, such as a solenoid coil, circular coil, spiral coil, planar coil, or frustum coil, for example. The sensor coil 108 may include wire of various thicknesses, and the sensor coil may be of different diameters, heights, and/or lengths. Variously sized coils may allow for varying spatial, temporal, and depth resolution. The sensor coil 108 may include a wire, such as a Litz wire, which may be insulated. The wire may be metal or other conductive material.

The inductive device 102 may include a plurality of sensor coils 108, such as two, three, four, five, or more sensor coils 108. The size and dimensions of the coil, including the diameter, may vary between the coils. For example, the sensor coils 108 may be of differing diameter and may be positioned concentrically about a central axis. For further example, there may be three sensor coils, where they have a small, medium, and large diameter respectively.

The inductive device 102 can further include a position gauge, which may record the location of the inductive device 102 on the chest 104 of the subject 105. The position gauge may be attached to the inductive device 102 and/or may be incorporated within the sensor unit 110, discussed below. The position gauge may include an accelerometer or gyroscope which operably connects to the sensor unit 110 to provide the sensor unit 110 with location information corresponding to parallel resistance values (or frequency loss or power loss data) at the given location on the chest 104.

The inductive device 102 may further include a temperature sensor, which may operably couple with the processor 124, discussed below. The temperature sensor may provide temperature data to the processor 124. The temperature data may correspond with a given location measured by the position gauge. As such a data set may be created which links position of the inductive device 102, temperature at the position, and diagnostic data (e.g. parallel resistance) measured at that position, and time within the time interval.

The inductive device 102 may include a sensor unit 110 of analog and digital processing components, with a resistive, inductive, and capacitive (RLC) circuit 112 and frequency counter 114. The sensor unit 110 may be operably connected to a computer 116. The sensor unit 110 may attach to the computer 116 via a cable 118, such as a USB cable, or alternatively may connect with a computer 116 wirelessly.

The inductive device 102 may further include a plurality of sensor units 110. For example, the inductive device 102 may include a plurality of sensor coils 108, each respectively connected with a sensor unit 110.

In prototypes, some of which are described in the figures, the Texas Instruments LDC (inductive to digital converter) 1101 chip was used to convert signals from coils into computer readouts. However, the sampling rate for this LCD 1101 frequency counter IC chip is limited to approximately 40 samples per second. In order to navigate this limitation, heterodyne downshifting was used for a higher frequency readout. If a higher sampling rate is required, the coil voltage can be connected to a frequency mixer and get downshifted to a lower frequency at approximately 1 kHz. Then the low-frequency signal is sampled by an analog-to-digital converter, bandpass-filtered, and conditioned by digital signal processing algorithms to recover the resonant frequency. This method allows a higher sampling rate above 200 samples per second.

The sensor unit 110 may include a memory 120. The memory 120 may store programming instructions and control values derived from prior measurements from the sensor coil 108. That is, data from previous measurements of chest cavities with the same or similar type of sensor coil 108 may be averaged or otherwise processed to distill normal ranges of frequency and power loss measurements for particular positions on the chest. Although different subjects have different chest characteristics and thus exhibit different magnetic inductances based on age, gender, demographics, and various health factors, there are normal ranges of inductance that are relatively stable. In various aspects, the memory 120 may further store information indicative of previous sensor coil 108 measurements of the same subject 106, such as to measure a change in a respiratory condition or a change in respiratory health since a previous scan, for example, since a previous medical visit.

The sensor unit 110 may include a processor 124 which may read and write from memory 120 and executes instructions described herein. The instructions may cause the processor 124 to read measured values from the power meter and frequency counter 114, compare them with control values associated with the chest location (e.g. from the position gauge), calculate deltas, and compare the deltas to positive and negative thresholds associate with the chest location to ascertain an exceedance.

A "delta" is a difference between two values, or as otherwise known in the art.

An "exceedance" includes a value that is above a maximum threshold or below a minimum threshold, or as otherwise known in the art. An exceedance can have a sign and a magnitude. The sign can indicate whether the exceedance is above a positive threshold or below a negative one.

The processor 124 may output to the computer 116 the exceedance itself or a simplified indication. Indicator 122 can light up or audibly emit a sound to tell an operator of the exceedance. Furthermore, a display 126 may show much more data or graphical representations of data to the operator. The display 126 may be a monitor of a computer 116 or may be a separate device. The processor 124, memory 120, and other elements can be incorporated on a commercial off-the-shelf board.

In various implementations, the processor 124 may output to the computer 116 frequency data from the frequency counter 114 and/or power monitoring data from the power meter. The processor 124 may output a parallel resistance value, which the processor 124 may calculate using one or both of the frequency data and/or power loss data.

According to various implementations, data provided to the computer 116 may be provided with corresponding location or position information. For example, data, such as frequency data, power loss data, exceedances, and/or parallel resistance data may be provided by the processor 124 to the computer 116 with the associated location on the chest 104 at which the given data was recorded by the inductive device 102. For example, the processor 124 may generate a matrix which pairs given position information with specific data (of various forms discussed above).

The processor 124 includes any type of miniature electronic device with arithmetic, logic, and/or control circuitry for performing central processing, or a general or specialized digital circuit that performs translation or reconveying of digital signals using logic or other components, or as otherwise known in the art. For example it can include a traditional processor, a programmable logic controller (PLC), etc.

In various aspects, the computer 116 may compute various pulmonary volume metrics, such as FEV1 and FVC. The computer 116 may further compute a respiratory rate. As discussed further below, these values may be "predicted" values, in that it is not a raw data measurement calculated from the subject 106 directly. Instead, based on the correlation between parallel resistance data from the inductive device 102 and various pulmonary volume metrics, a given metric may be predicted based at least in part on the parallel resistance values received by the inductive device 102.

The computer 116 may further compare the parallel resistance detected by the inductive device 102 to various known parallel resistance values. Similarly, the computer 116 may calculate various "predicted" pulmonary volume metrics, and/or a respiratory rate, as discussed, and compare such metrics with known pulmonary volume metrics. These "historical" pulmonary volume metrics, may be stored within the memory 120 and recalled by the computer 116 for such comparisons. In various implementations, the computer 116 may determine an initial prognosis or diagnosis based on the various comparisons discussed herein.

The inductive device 102 may further include a scaffold 128 to support the sensor coil 108. the scaffold 128 may be plastic or other material to provide physical strength and rigidity to the sensor coil 108 and assist the sensor coil 108 in maintaining shape.

The inductive device 102 may further include magnetic shielding 130. The magnetic shielding 130 may be used to protect the sensor coil 108 from internal or external signals. The magnetic shielding 130 may be of any size, thickness, or material so long as it serves the purpose of increasing the signal-to-noise ratio or improving characteristics of the inductive device 102. In various aspects, the magnetic shielding 130 may be ferrite shielding and may be placed around the sensor coil 108.

In testing the inductive device 102 with and without the magnetic shielding 130, results demonstrated that the resonant frequency does not change, meaning the stray capacitance coupled from the sensor coil 108 to the human tissue does not dominate. Meanwhile, the main difference is the decrease in Rp at the resonant frequency, which originates from the energy loss caused by the eddy currents generated in the conductive human tissue.

The inductive device 102 may further include a nonconductive base 132. The nonconductive base 132 may be made of plastic or similar material. the nonconductive base 132 may provide a structure in which the components of the inductive device are secured. Further, the nonconductive base may provide an attachment for the sensor unit 110.

Figure 2A:
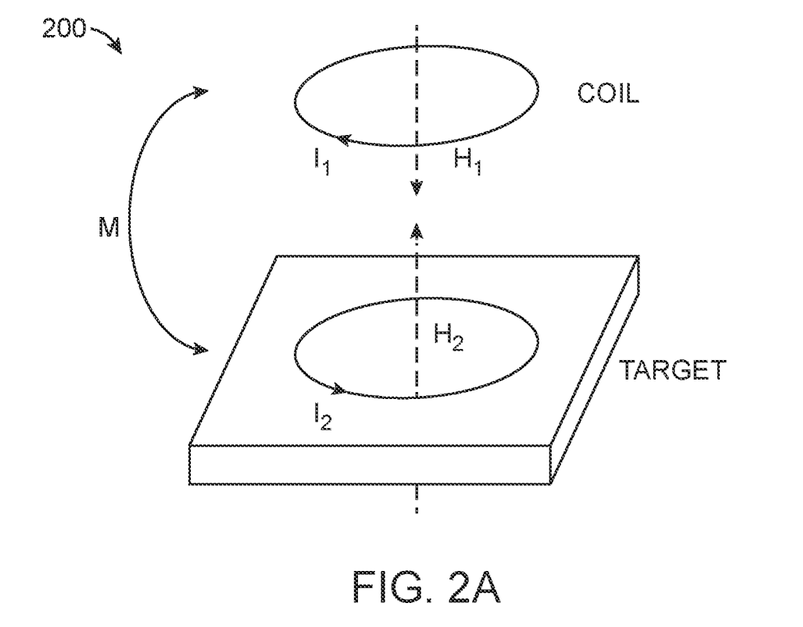
FIG. 2A illustrates an exemplary magnetic coupling in a model of a sensor coil and target according to various implementations of the present disclosure.

FIG. 2A illustrates magnetic coupling in a model 200 of a sensor coil 108 and target 202 in accordance with an embodiment. The sensor coil 108 is modeled as having current $i_1$ and producing magnetic field $H_1$. This creates magnetic coupling M between the sensor coil 108 and the target 202. The target 202 may be the chest 104 of a subject 106, modeled as a flat, two-layer structure with its own current $i_2$ and induced magnetic field $H_2$. Note that currents $i_1$ and $i_2$ are in opposite directions.

Figure 2B:
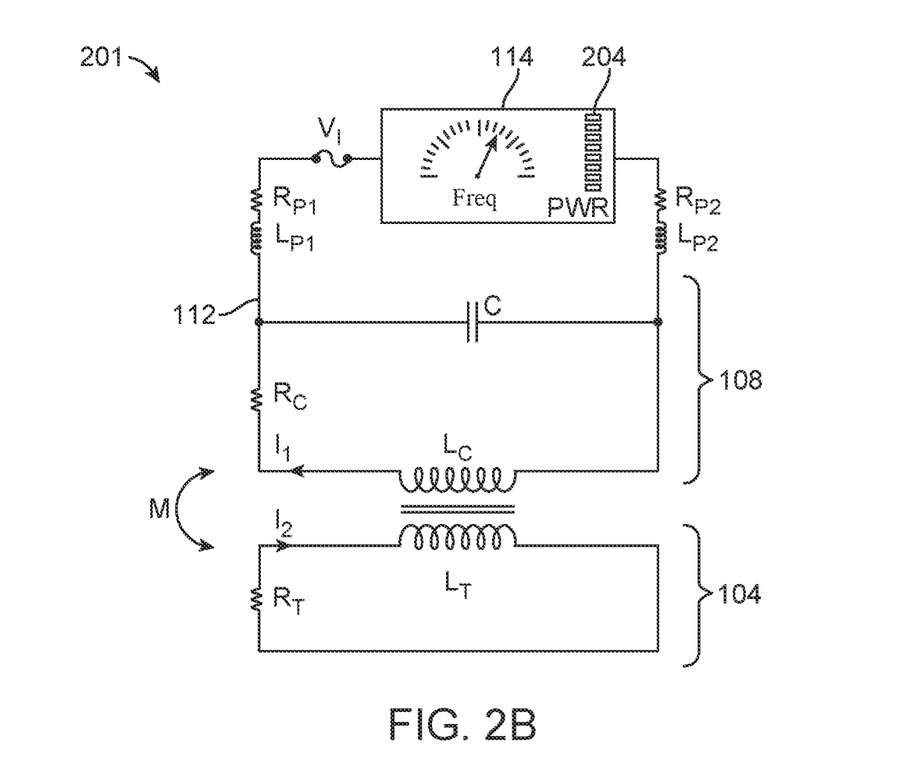
FIG. 2B illustrates an equivalent circuit for the model of FIG. 2A.

FIG. 2B illustrates equivalent circuits 201 for the model 200 in FIG. 2A. RLC circuit 112 includes a sensor coil 108 modeled with current $i_1$ running through inductor Lc with resistance Rc and capacitance C. The sensor coil 108 may be connected to a voltage source providing Vi alternating current. Parasitics of connections are modeled as resistances $R_{p1}$ and $R_{p2}$ and inductances $L_{p1}$ and $L_{p2}$.

Frequency counter 114 and power meter 204 are shown, from which measured values can be taken, recorded, compared, and used to indicate anomalies. Data may be converted in an analog-to-digital (A/D) converter and provided to a computer 116.

The sensor coil 108 is connected through magnetic coupling M to the chest 104 of a subject 106. The chest 104 may include eddy current $i_2$ running through an idealized resistor Rt (target) and inductor Lt.

In various embodiments the sensor apparatus 100 may be utilized to provide diagnostics to various areas of the chest 104. Scanning using the inductive device may be static or dynamic.

Static scanning may include positioning the inductive device 102 at a location on the chest 104 and maintaining the inductive device 102 at that location for a time interval. In various implementations, this time interval may be for a single breath or multiple breaths. For example, the inductive device 102 may include a sensor coil 108 which is configured to measure parallel resistance over a wide area of the chest 104. For further example, the inductive device 102 may be placed near the center of the chest 104, such as near the middle of the sternum. In such a configuration the inductive device 102 may scan a large area of both lungs from a single placement site.

Static scanning may further include positioning the inductive device 102 at a plurality of other locations on the chest and repeating scanning for additional time intervals. For example, the sensor coil 108 may be configured to scan a smaller area of the chest 104 at each location. For further example, static scanning may include scanning one or more locations on the chest 104 for each side of the chest (corresponding to each lung). Static scanning may be performed at a plurality of locations on each side of the chest 104, for example at one to twenty locations, and any number of locations therebetween.

Where multiple scans are taken at a number of locations on the chest 104, data recorded at each scan location may overlap, at least in part. As such, the computer 116 and/or the processor 124 may be configured to recognize the overlap between a plurality of scans and combine or otherwise eliminate duplicate data.

Figure 3A:
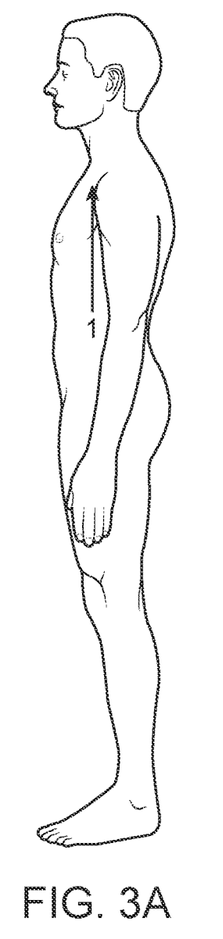
FIG. 3A illustrates an exemplary dynamic scanning path on a subject's chest according to various implementations of the present disclosure.
Figure 3B:
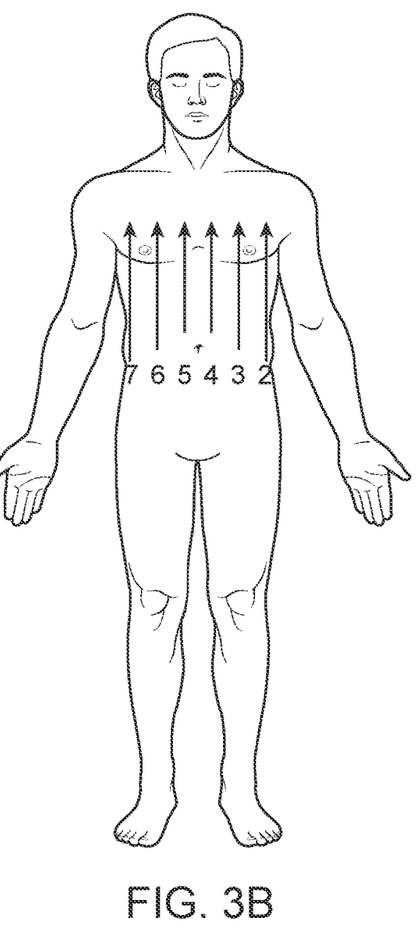
FIG. 3B illustrates further exemplary dynamic scanning paths on a subject's chest continued from FIG. 3A.
Figure 3C:
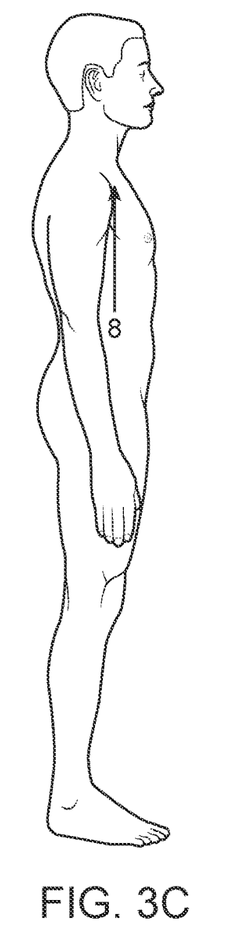
FIG. 3C illustrates a further exemplary dynamic scanning path on a subject's chest continued from FIG. 3B.

FIGS. 3A-3C illustrate exemplary dynamic scanning paths (1-8) on the chest 104 of a subject 106. Dynamic scanning may involve continuously moving the inductive device 102 linearly across the chest 104 while performing the scan. As shown in FIGS. 3A-3C, 8 equidistant paths may be selected across the sides and front of the chest. Specifically path 1 represents a dynamic scan path on the left mid-axillary of the subject 106. Paths 2-7 may be equidistant dynamic scan paths across the front of the chest of the subject 106.

Data recorded from the 8 paths may be normalized and combined to create a heatmap or similar mapping display of a two-dimensional representation of the parallel resistance at various points across the chest 104 of the subject 106. For example, the heatmap may have a color or shade coding (e.g. light to dark, blue to red, etc.) to represent a scale between varying parallel resistance values, such as more conductive regions (i.e. those with lower parallel resistance) and less conductive regions (i.e. those with higher parallel resistance) of the chest 104. For example, more conductive regions may be shown brighter, while less conductive regions may be shown darker.

While dynamic scanning is shown herein as having 8 scan paths, it should be understood that a wide range of paths may be used, either less or more than eight, without departing from the concepts herein. Furthermore, while shown as vertical paths which are equidistant, other implementations may utilize horizontal paths and may otherwise vary the spacing between each path.

Figure 4:
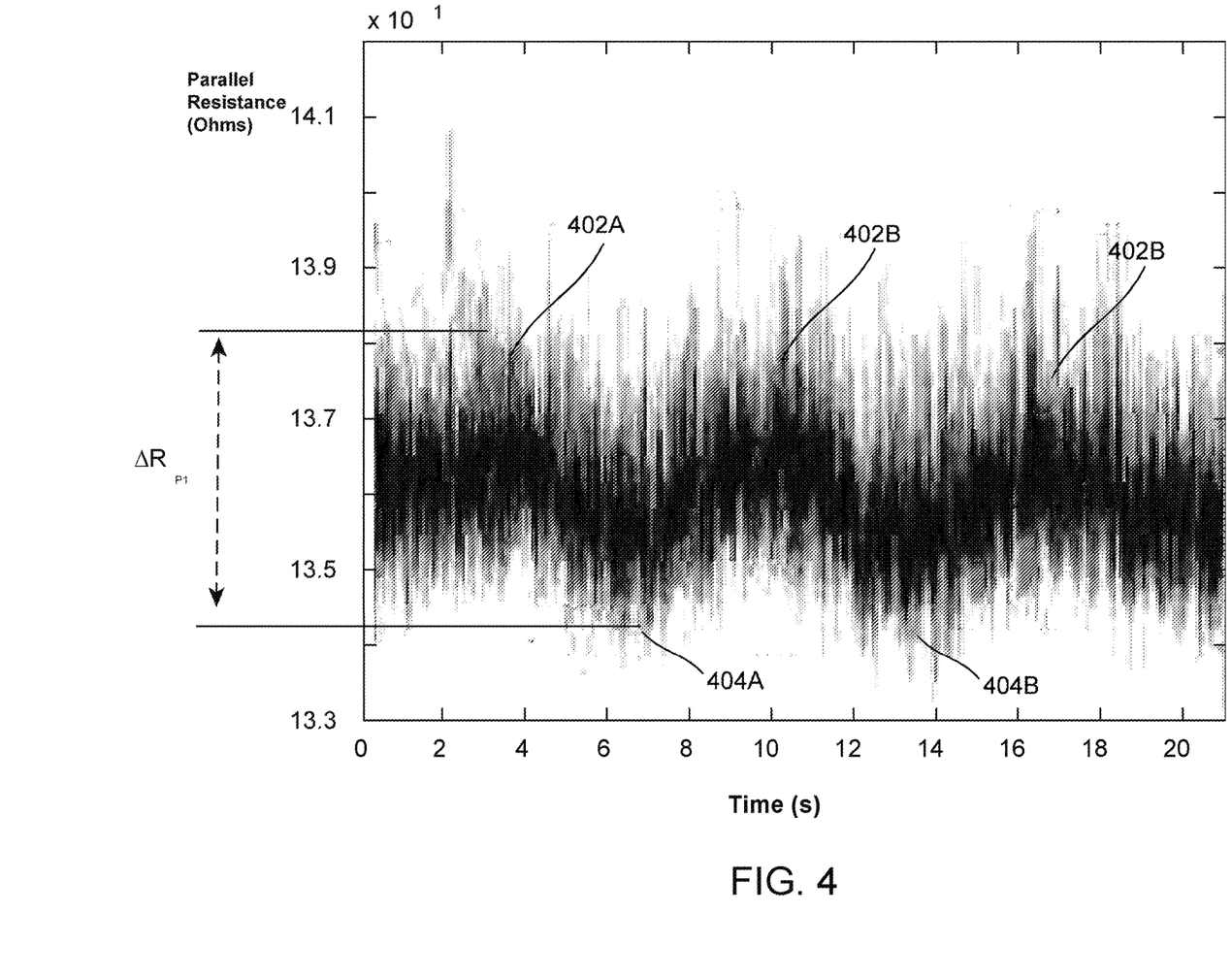
FIG. 4 illustrates an exemplary unfiltered pulmonary waveform of measured parallel resistance over a time interval according to various implementations of the present disclosure.

FIG. 4 illustrates an exemplary unfiled pulmonary waveform of measured parallel resistance ($R_n$) over a time interval according to various implementations of the present disclosure. As shown, as a subject breathes, parallel resistance changes with time. The unfiltered data recorded from the inductive device 102 may be plotted graphically over time. In general, parallel resistance at a crest 402 corresponds with an inhale and the parallel resistance at a trough 404 corresponds with an exhale. As such, a delta in parallel resistance can be measured for each breath between a given crest 402 and trough 404. For example, a first delta in parallel resistance ($AR_{p1}$) may be measured by taking the difference between the first crest 402A and the first trough 404A. Similarly, a second delta in parallel resistance ($AR_{p2}$) may be calculated between a second crest 402B and a second trough 404B. A third delta in parallel resistance ($AR_{p3}$) may be calculated between a third crest 402C and a third trough 404C. A plurality of deltas may be calculated based on the number of breaths recorded. Based on the deltas in parallel resistance an average parallel resistance ($\Delta R_p$) may be calculated by adding the deltas together and dividing by the number of deltas averaged. This average parallel resistance ($\Delta R_p$) may provide further accuracy in determining the pulmonary function of the subject compared to basing lung function off a single breath.

Figure 5:
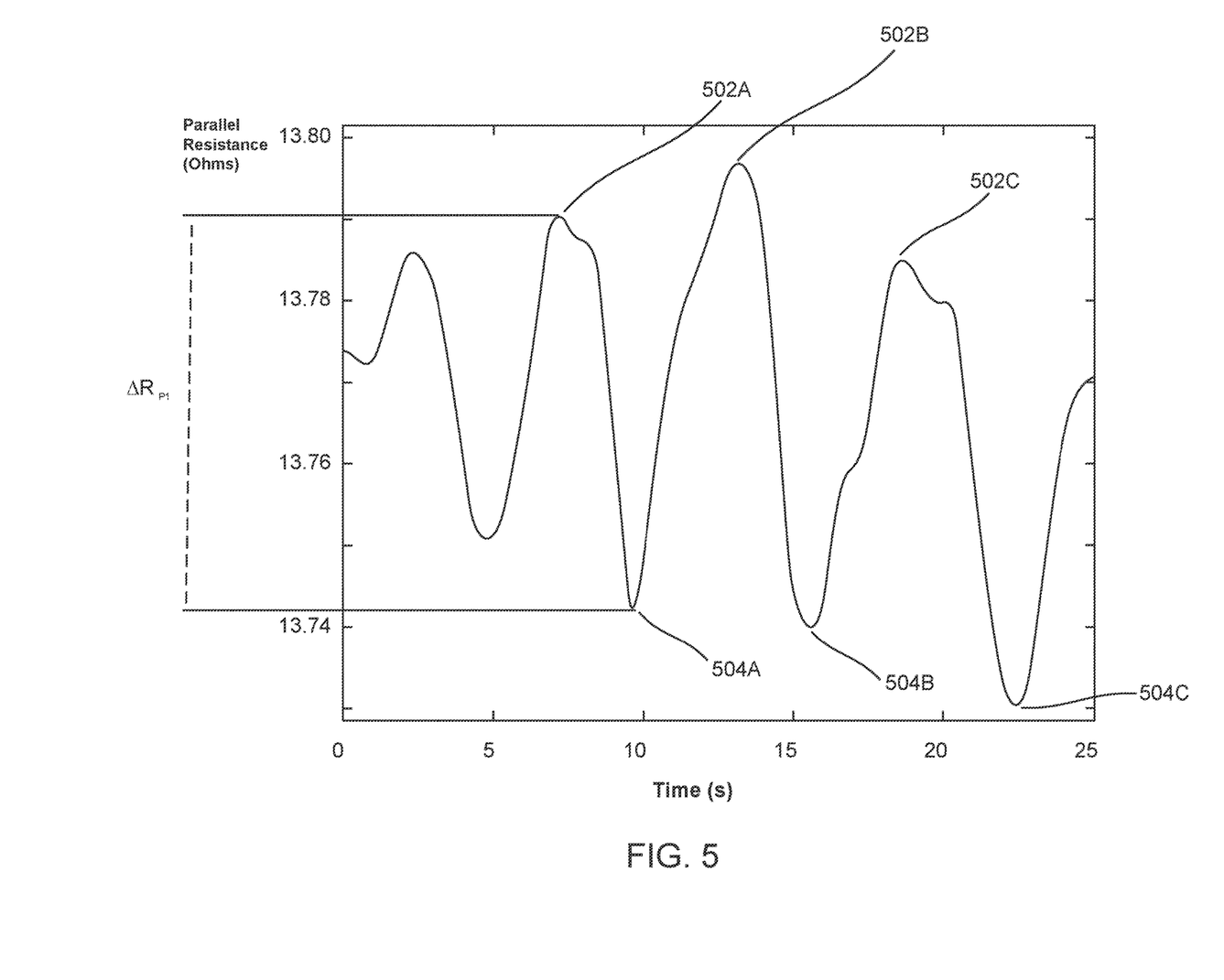
FIG. 5 illustrates an exemplary filtered pulmonary waveform of measured parallel resistance over a time interval according to various implementations of the present disclosure.

FIG. 5 illustrates an exemplary filter pulmonary waveform of measured parallel resistance over a time interval, according to various implementations of the present disclosure. An unfiltered waveform, such as the waveform of FIG. 4 may be filtered to remove high frequency noise. For example, Savitzky-Golay and simple Gaussian filters, such as those from MATLAB Signal Processing Toolbox may be used to remove high frequency noise.

A similar process of determining a plurality of deltas in parallel resistance ($\Delta R_p$) for each breath may be applied to the filtered pulmonary waveform as was described regarding FIG. 4 previously. The filtered pulmonary waveform may provide easier location of a maximum and minimum parallel resistance for each breath, thus allowing for a more precise calculation of the delta in parallel resistance ($AR_p$). For example, a first delta in parallel resistance ($AR_{p1}$) may be measured by taking the difference between the first crest 502A and the first trough 504A. Similarly, a second delta in parallel resistance ($AR_{p2}$) may be calculated between a second crest 502B and a second trough 504B. A third delta in parallel resistance ($AR_{p3}$) may be calculated between a third crest 502C and a third trough 504C. A plurality of deltas may be calculated based on the number of breaths recorded. Based on the deltas in parallel resistance an average parallel resistance ($\Delta R_p$) may be calculated by adding the deltas together and dividing by the number of deltas averaged. This average parallel resistance ($\Delta R_p$) may provide further accuracy in determining the pulmonary function of the subject compared to basing lung function off a single breath.

Figure 6A:
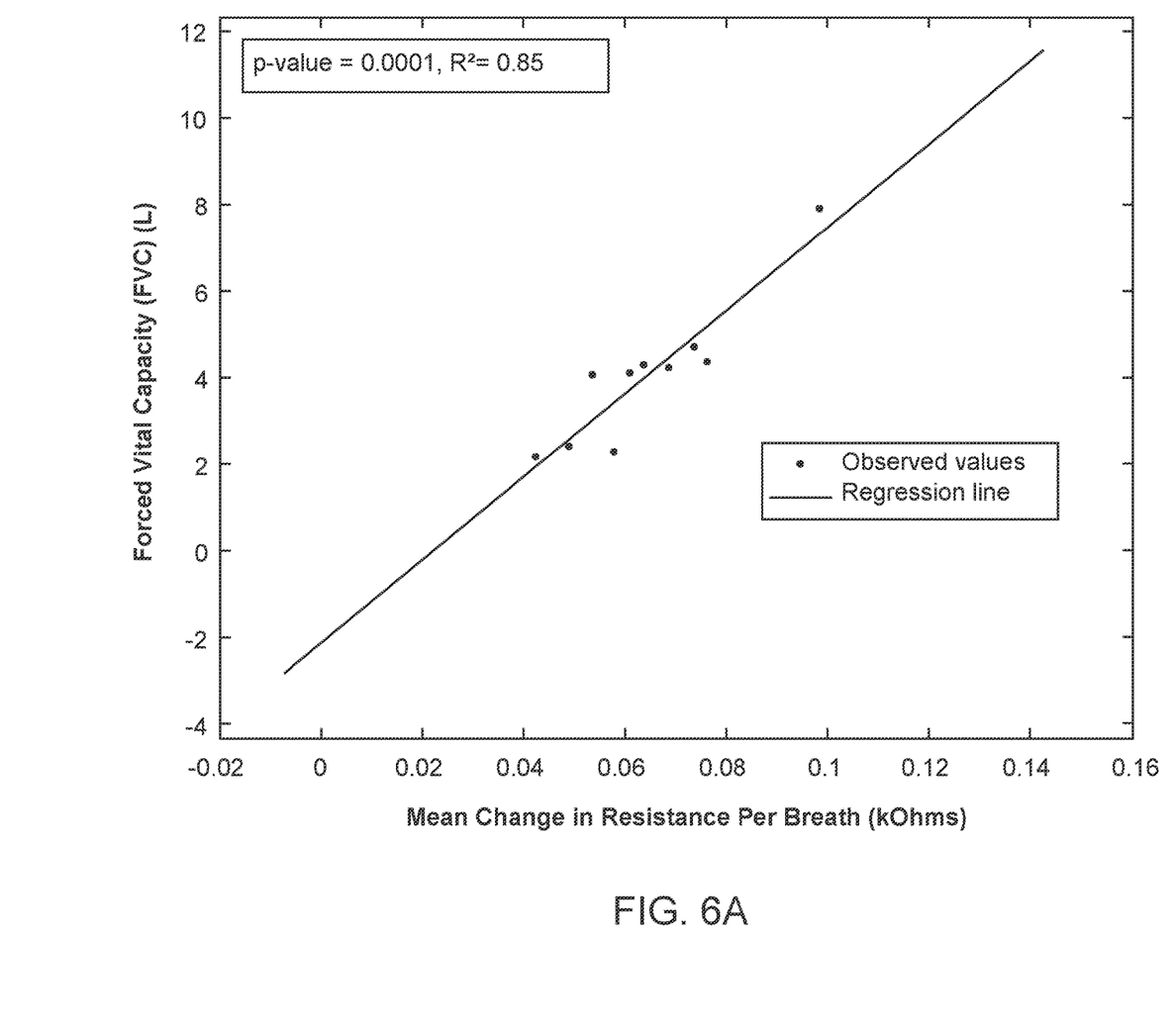
FIG. 6A illustrates an exemplary linear regression analysis correlating mean change in parallel resistance per breath and FVC according to various implementations of the present disclosure.
Figure 6B:
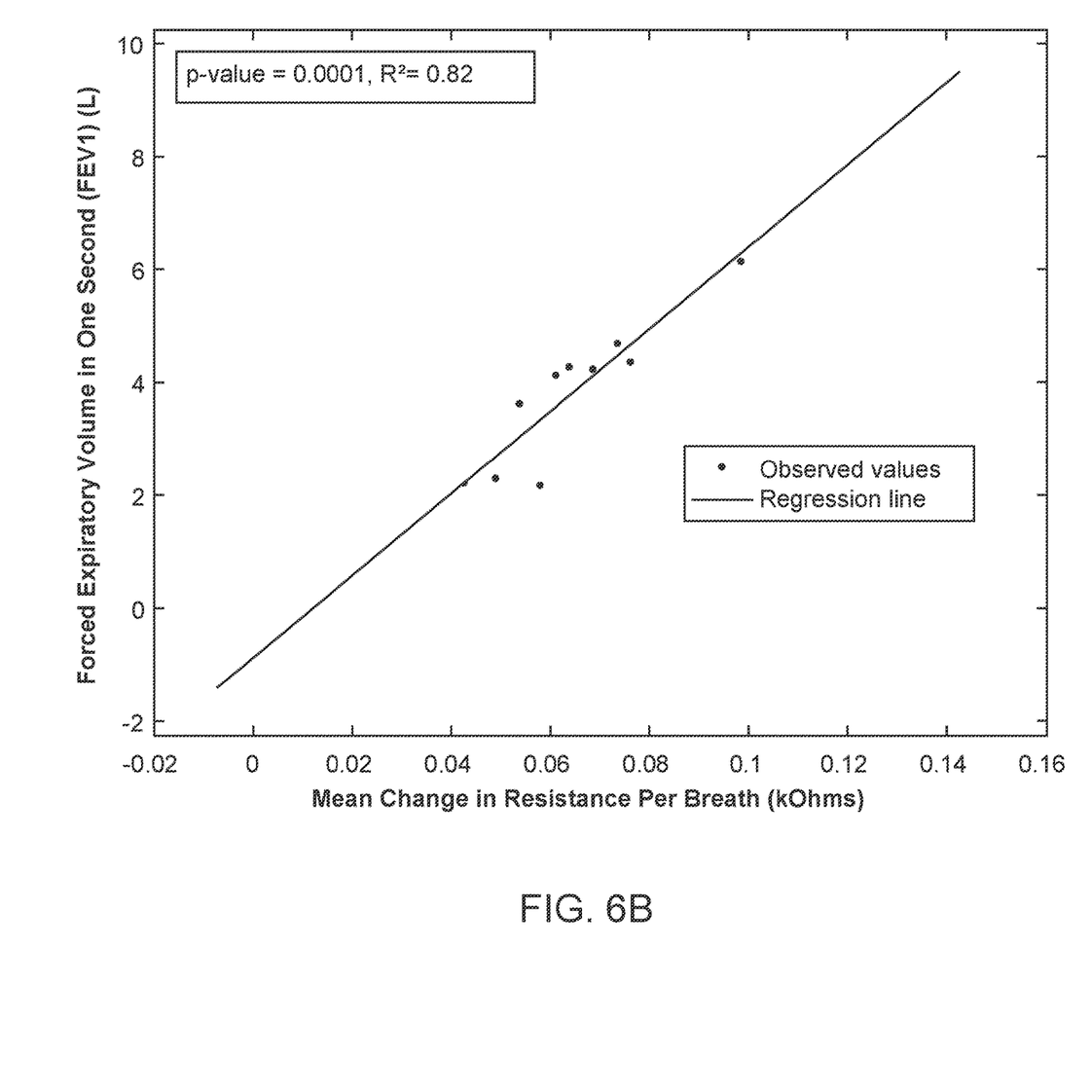
FIG. 6B illustrates an exemplary linear regression analysis correlating mean change in parallel resistance per breath and FEV1 according to various implementations of the present disclosure.
Figure 6C:
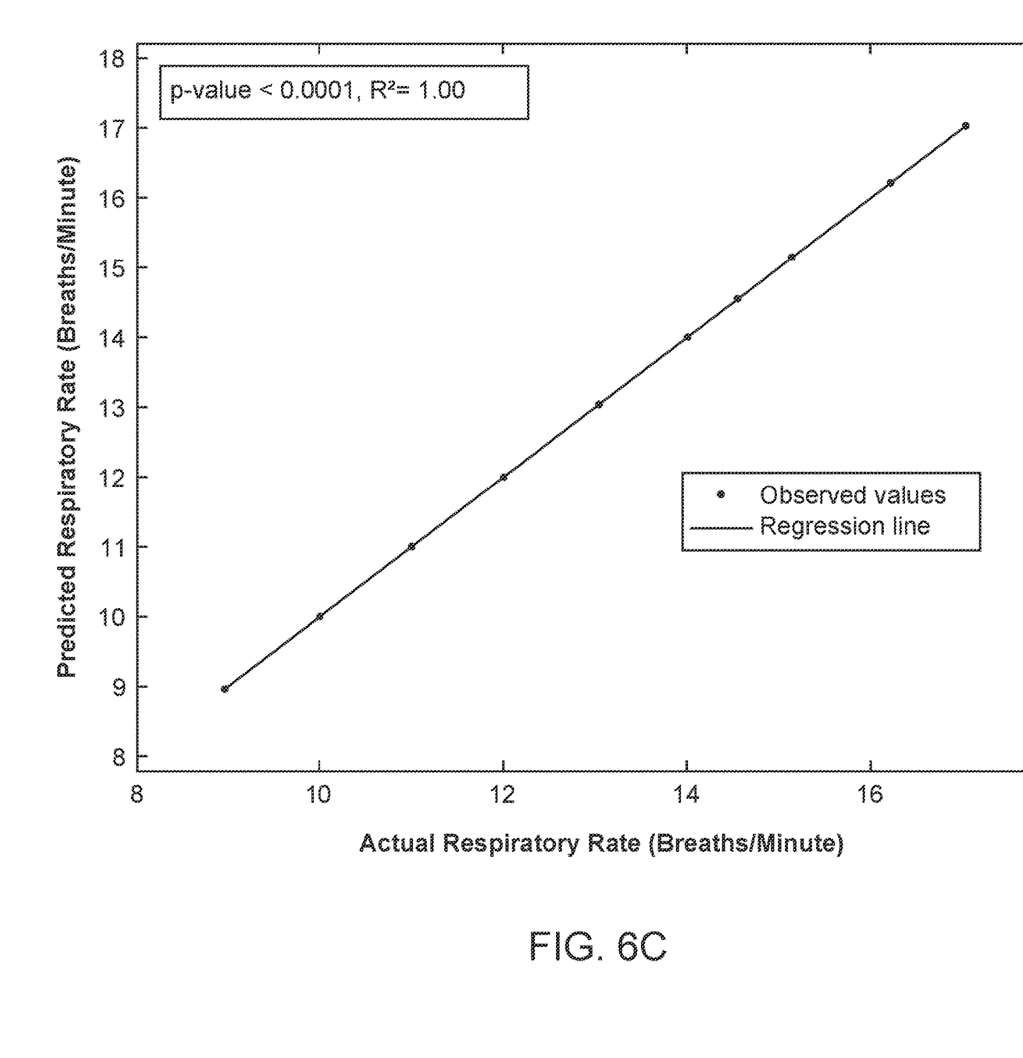
FIG. 6C illustrates an exemplary linear regression analysis correlating a predicted respiratory rate (based on the parallel resistance values) and an actual respiratory rate.

FIGS. 6A-6C illustrate exemplary linear regression analysis correlating mean change in parallel resistance per breath with FVC, FEV1, and respiratory rate, respectively. Linear regression analysis demonstrates the strength of correlation between the parallel resistance values measured by the sensor apparatus 100 compared to pulmonary volume metrics to determine whether the sensor apparatus 100 provides a strong predictor for such measurements.

FIG. 6A shows the linear regression analysis of parallel resistance per breath with FVC. A statistical p-value and goodness-of-fit ($R^2$) value are provided for the linear regression. Given the ten test subjects, the $R^2$ was 0.85.

FIG. 6B shows the linear regression analysis of parallel resistance per breath with FEV1. A statistical p-value and goodness-of-fit ($R^2$) value are provided for the linear regression. Given the ten test subjects, the $R^2$ was 0.82.

FIG. 6C shows the linear regression analysis of predicted respiratory rate (based on parallel resistance recorded) and actual respiratory rate. A statistical p-value and goodness-of-fit ($R^2$) value are provided for the linear regression. Given the ten test subjects, the $R^2$ was 1.00.

As can be seen, for the given subjects in the study, the greatest predictive value from the parallel resistance recorded was the respiratory rate, at 0.99 the correlation is nearly perfect. With respect to pulmonary volume metrics, regression analysis demonstrated that mean change in $R_p$ per breath was closely correlated with $FEV_1$ and FVC.

Figure 7:
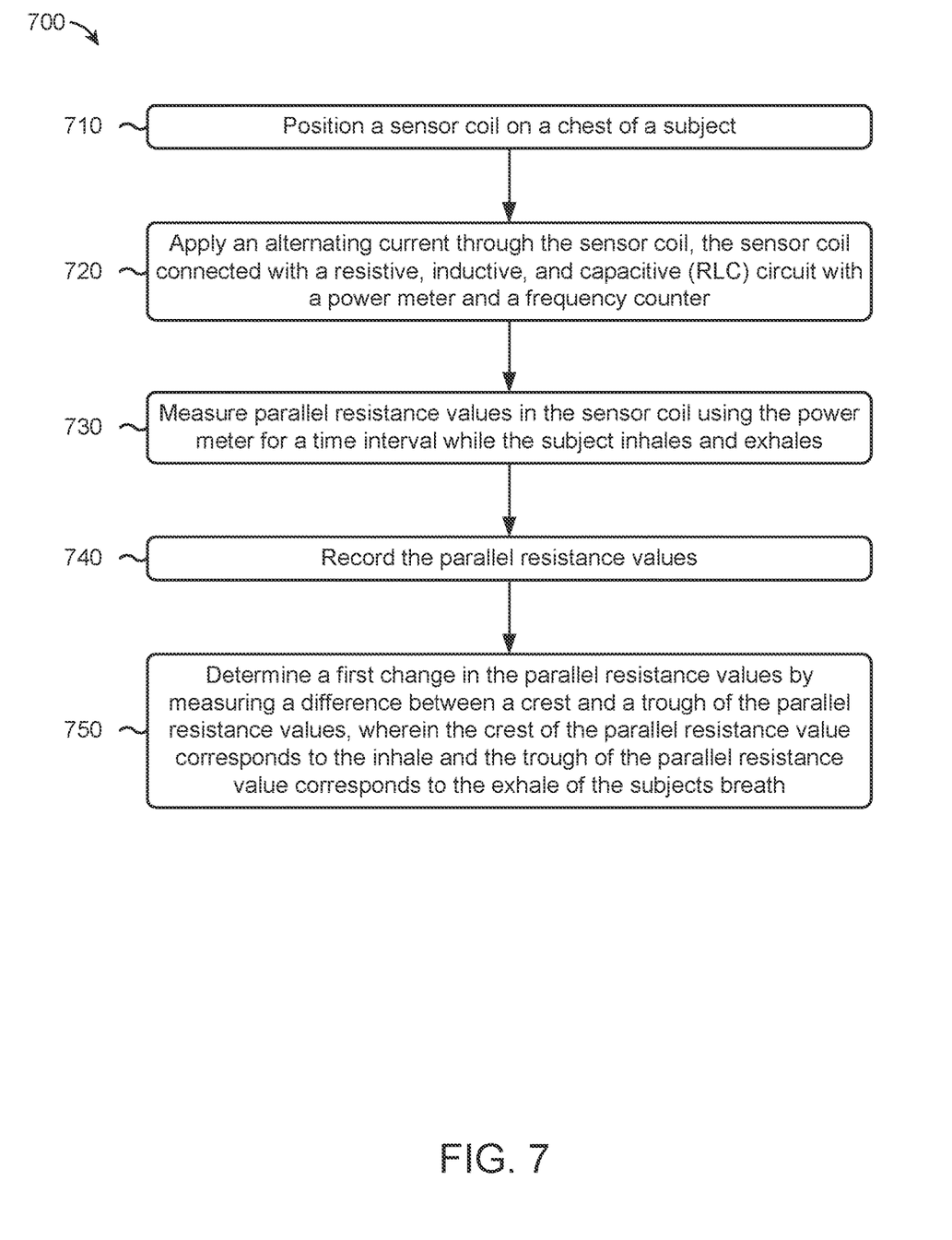
FIG. 7 illustrates a flowchart of an exemplary process of medical diagnosis and testing of the pulmonary function according to various implementations of the present technology.

FIG. 7 illustrates an exemplary flowchart of an example process 700 of medical diagnosis and testing of the pulmonary function according to various implementations of the present technology. In some implementations, one or more process blocks of FIG. 7 may be performed by a medical professional (e.g. a doctor, physician, or medical assistant), or other human. In some implementations, one or more process blocks of the figure may be performed by a computer controlled device, including for example an automated or semi-automated, computer controlled device (e.g. a robot). Additionally, or alternatively, one or more process blocks of FIG. 7 may be performed by one or more components of sensor unit 110, such as for example processor 124, memory 120, and/or by one or more components of the sensor apparatus 100, including for example the computer 116.

At block 710, the process 700 may include positioning a sensor coil 108 on a chest 104 of a subject 106. For example, an operator or an automated machine (e.g. a robot) may position a sensor coil on a chest 104 of a subject 106. The process may further include determining a location or a plurality of locations at which the parallel resistance values are measured. For example, the process 700 may include determining a second location at which the parallel resistance values are measured, and positioning the sensor coil 108 on the chest 104 of a subject 106 at the second location. In various aspects, positioning of the sensor coil 108 may be performed manually (such as with an operator's hand). In other aspects, the positioning may be performed by a robotic system.

At block 720, the process 700 may include applying a current (e.g. an alternating current) through the sensor coil 108, the sensor coil 108 may be connected with a resistive, inductive, and capacitive (RLC) circuit 112 with a power meter 204 and a frequency counter 114. For example, the inductive device 102 may apply a current through the sensor coil 108, as described above.

At block 730, the process 700 may include measuring parallel resistance values in the sensor coil 108 using the power meter 204 for a time interval while the subject 106 inhales and exhales. For example, the inductive device 102 may measure parallel resistance values in the sensor coil 108 using the power meter 204, as described above. During the time interval, the subject 106 may perform one inhale and one exhale or may perform a plurality of inhales and a plurality of exhales.

At block 740, the process 700 may include recording the parallel resistance values. The parallel resistance values may be stored within the memory 120 of the sensor unit 110, or may be communicated and stored within the computer 116, for example.

At block 750, the process 700 may include determining a first change (e.g. first delta) in the parallel resistance values by measuring a difference between a crest (e.g. 402A, 502A) and a trough (e.g. 404A, 504A) of the parallel resistance values, wherein the crest of the parallel resistance value corresponds to the inhale and the trough of the parallel resistance value corresponds to the exhale of the subjects breath. For example, the inductive device 102 may determine a first change (e.g. first delta) in the parallel resistance values by measuring a difference between a crest and a trough of the parallel resistance values, wherein the crest of the parallel resistance value corresponds to the inhale and the trough of the parallel resistance value corresponds to the exhale of the subjects breath, as described above.

In various aspects, the process 700 may include determining a second change in the parallel resistance values by measuring a difference between a second crest (e.g. 402B, 502b) and a second trough (e.g. 404B, 504B) of the parallel resistance values, wherein the second crest of the parallel resistance value corresponds to a second inhale of the plurality of inhales and the trough of the parallel resistance value corresponds to a second exhale of the plurality of exhales. In various aspects, the process 700 may include determining an average between the first change and the second change in the parallel resistance values. The process 700 may include calculating a forced vital capacity (FVC), a forced expiratory volume in one second (FEV1), or a respiratory rate using the plurality of crests and plurality of troughs of the sinusoidal function.

In various aspects, the process 700 may include calculating a forced vital capacity (FVC), a forced expiratory volume in one second (FEV1), or a respiratory rate using the change in parallel resistance values. The process 700 includes diagnosing a respiratory problem based at least in part on the change in parallel resistance values.

The process 700 may include comparing the parallel resistance values with historical parallel resistance values, and diagnosing a respiratory problem based at least in part on the comparison. In one aspect the process may include comparing the FVC, the FEV1, or the respiratory rate with respective FVC historical values, FEV1 historical values, or respiratory rate historical values, and diagnosing a respiratory problem based at least in part on the comparison.

In various aspects, the process 700 may further include the sensor coil 108 and RLC circuit 112 being connected with a frequency counter 114, and the process 700 may further include measuring oscillation frequency values of the RLC circuit 112 during the time interval, recording the oscillation frequency values, determining a change in the oscillation frequency values by measuring a difference between a crest and a trough of the oscillation frequency values, wherein the crest of the oscillation frequency value corresponds to the inhale and the trough of the oscillation frequency value corresponds to the exhale of the subjects breath, and correlating the change in oscillation frequency values with the change in the parallel resistance values.

In various aspects, the parallel resistance values with at least one signal filter to remove high frequency noise to create a sinusoidal function with the parallel resistance values over time, wherein the sinusoidal function has a plurality of crests and a plurality of troughs.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" in reference to a temperature or other engineering units includes measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method of diagnosing respiratory problems in lungs of a subject, the method comprising:
   positioning a sensor coil on a chest of a subject;
   applying an alternating current through the sensor coil, the sensor coil connected with a resistive, inductive, and capacitive (RLC) circuit with a power meter and a frequency counter;
   measuring parallel resistance values in the sensor coil using the power meter for a time interval while the subject inhales and exhales;
   recording the parallel resistance values;
   determining a first change in the parallel resistance values by measuring a difference between a crest and a trough of the parallel resistance values, wherein the crest of the parallel resistance value corresponds to the inhale and the trough of the parallel resistance value corresponds to the exhale of the subject's breath; and
   calculating a forced vital capacity (FVC) or a force expiratory volume in one second (FEV1) using the change in parallel resistance values.

2. The method of claim 1, further comprising:
   diagnosing a respiratory problem based at least in part on the change in parallel resistance values.

3. The method of claim 1, further comprising:
   comparing the parallel resistance values with historical parallel resistance values; and
   diagnosing a respiratory problem based at least in part on the comparison.

4. The method of claim 1, further comprising:
   comparing the FVC or the FEV1 with respective FVC historical values or FEV1 historical values; and
   diagnosing a respiratory problem based at least in part on the comparison.

5. The method of claim 1, further comprising:
   determining a location at which the parallel resistance values are measured.

6. The method of claim 5, further comprising:
   determining a second location at which the parallel resistance values are measured; and
   positioning the sensor coil on the chest of a subject at the second location.

7. The method of claim 6, wherein the positioning is performed by a robotic system.

8. The method of claim 1, wherein during the time interval the subject performs a plurality of inhales and a plurality of exhales.

9. The method of claim 8, further comprising:
   determining a second change in the parallel resistance values by measuring a difference between a second crest and a second trough of the parallel resistance values, wherein the second crest of the parallel resistance value corresponds to a second inhale of the plurality of inhales and the trough of the parallel resistance value corresponds to a second exhale of the plurality of exhales.

10. The method of claim 9, further comprising:
    determining an average between the first change and the second change in the parallel resistance values.

11. The method of claim 1, further comprising:
    measuring oscillation frequency values of the RLC circuit during the time interval;
    recording the oscillation frequency values;
    determining a change in the oscillation frequency values by measuring a difference between a crest and a trough of the oscillation frequency values, wherein the crest of the oscillation frequency value corresponds to the inhale and the trough of the oscillation frequency value corresponds to the exhale of the subject's breath; and
    correlating the change in oscillation frequency values with the change in the parallel resistance values.

12. The method of claim 1, further comprising:
    processing the parallel resistance values with at least one signal filter to remove high frequency noise to create a sinusoidal function with the parallel resistance values over time, wherein the sinusoidal function has a plurality of crests and a plurality of troughs.

13. The method of claim 12, further comprising:
    calculating the FVC or FEV1 using the plurality of crests and plurality of troughs of the sinusoidal function.

14. The method of claim 1, further comprising:
    performing a linear regression analysis between the parallel resistance values and an independently measured FVC; and
    calculating a p-value or goodness-of-fit ($R^2$) for the linear regression analysis.

15. The method of claim 1, further comprising:
    performing a linear regression analysis between the parallel resistance values and an independently measured FEV1; and calculating a p-value or goodness-of-fit ($R^2$) for the linear regression analysis.

16. A method of scanning lungs of a subject, the method comprising:
- moving a sensor coil across a chest of a subject;
- applying an alternating current through the sensor coil, the sensor coil connected with a resistive, inductive, and capacitive (RLC) circuit with a power meter and a frequency counter;
- measuring parallel resistance values in the sensor coil using the power meter for a time interval while the subject inhales and exhales;
- recording the parallel resistance values; and
- displaying a two-dimensional representation based on the parallel resistance values.

* * * * *